United States Patent [19]

Takahashi et al.

[11] Patent Number: 4,868,403
[45] Date of Patent: Sep. 19, 1989

[54] SURFACE INSPECTING APPARATUS

[75] Inventors: Ippei Takahashi; Akihisa Iida, both of Shizuoka, Japan

[73] Assignee: Fuji Photo Film Co., Ltd., Kanagawa, Japan

[21] Appl. No.: 147,710

[22] Filed: Jan. 25, 1988

[30] Foreign Application Priority Data

Jan. 23, 1987 [JP] Japan .................................. 62-13461

[51] Int. Cl.$^4$ ............................................ G01N 21/88
[52] U.S. Cl. ..................................... 250/563; 356/431
[58] Field of Search ............... 250/562, 563, 571, 572; 356/430, 431, 445, 447

[56] References Cited

U.S. PATENT DOCUMENTS

| 3,618,063 | 11/1971 | Johnson | 250/563 |
| 4,134,684 | 1/1979 | Jette | 356/430 |
| 4,509,076 | 4/1985 | Yoshida | 250/563 |
| 4,546,444 | 10/1985 | Bullis | 356/431 |

Primary Examiner—David C. Nelms
Attorney, Agent, or Firm—Young & Thompson

[57] ABSTRACT

An apparatus for inspecting the surface of web material moving lengthwise at a constant speed by scanning the surface in the direction of the width of the surface with a light beam. The scanned beam modulated by the surface is received and converted into an electric signal which is divided into division signals representing divisions of the width of the web. A first memory capability is provided for storing division signals added together by division every N transverse scans. The added division signals are transferred to a second memory capability by division, for evaluating the surface defect distribution of the scanned surface division by division.

4 Claims, 3 Drawing Sheets

SURFACE INSPECTING APPARATUS

BACKGROUND OF THE INVENTION

The present invention relates to an apparatus for inspecting a surface of a web material continuously moving lengthwise by scanning the surface in the direction of the width of the web material with a light beam so as to detect surface defects of the web material.

Various apparatus are well known for scanning a surface of a continuously running web material, such as films, paper sheets, thin plates or the like, with a scanning beam in the direction of the width of the web material to detect surface defects of the web material. Some of these surface scanning apparatus utilize a photoelectric light detector which is adapted to receive light modulated by surface defects to provide defect signals. Based on the defect signals a judgment is made as to whether the web material has unacceptable surface defects. Because they are non-contact devices and permit high speed surface defect detection, these surface inspection apparatus can be used in a web material production line.

One such surface inspection apparatus of the type utilizing a scanning beam and a photoelectric light detector is disclosed in Japanese Patent Publ. No. 56-39,419. The surface inspection apparatus disclosed therein is adapted to store data as to the surface defects of a web material and the positions of the surface defects in memories or shift registers every transverse scan. After the storage of the data for several transverse scans, the web material is evaluated based on these data by the aid of a computerized evaluation system.

A problem with such surface inspection apparatus is that the efficiency of inspection depends on the memory capacity because data on surface defects are memorized in the memory every transverse scan. For example, if the surface inspection apparatus can scan a web material in the direction of the width of the web material about 3,000 times per second, 3,000 memories can memorize only the data obtained for one second. Therefore, when inspecting the web material running at a speed of 60 m/min, data on surface defects only for one meter of the web material can be memorized in the 3,000 memories. On the other hand, if the web material to be inspected by the surface inspection apparatus runs at a slow speed of movement, a considerably greater number of memories are needed to memorize data on surface defects for a predetermined length of the web material.

OBJECT OF THE INVENTION

It is, therefore, an object of the present invention to provide a surface inspection apparatus which needs only a relatively small number of memories for memorizing data on surface defects of a web material to be inspected and is simple in construction.

SUMMARY OF THE INVENTION

The above object of the present invention is accomplished by providing a surface inspection apparatus comprising means for scanning a web material running lengthwise, in the direction of the width of the web material, with a light beam, the web material being spatially divided into smaller divisions in the scanning direction; light receiving means for receiving light modulated by a surface of the web material to provide division signals; first memory means for storing therein the division signals added together by division for a predetermined length of the web material; and second memory means to which the division signals added together by division are transferred from the first memory means every predetermined length of the web material. The added division signals are read out from the second memory to evaluate the surface defects of the web material based thereon by the aid of a computerized system.

According to a preferred embodiment of the surface inspection apparatus of the present invention, the added division data on surface defects of the predetermined length of the web material are transferred from the first to the second memory by actuating a switching means disposed between the first and second memory means each time a predetermined number of transverse scans of the web material has been effected. During the time the division data in the second memory are read out to evaluate the surface, data on surface defects of the following part of the web material are stored in the first memory. Owing to this transmission of the data obtained for the predetermined length of the web material it is possible to utilize only a small number of memories to memorize defect signals for a predetermined length of the web material so as to detect exactly surface defects of the web material independently of the transverse scanning speed and the web material linear speed and, furthermore, to construct the surface inspection apparatus simply and at a low manufacturing cost.

BRIEF DESCRIPTION OF THE DRAWINGS

This invention will be described with reference to its embodiment shown in the accompanying drawings wherein.

DETAILED DESCRIPTION OF THE INVENTION

Figure 1:
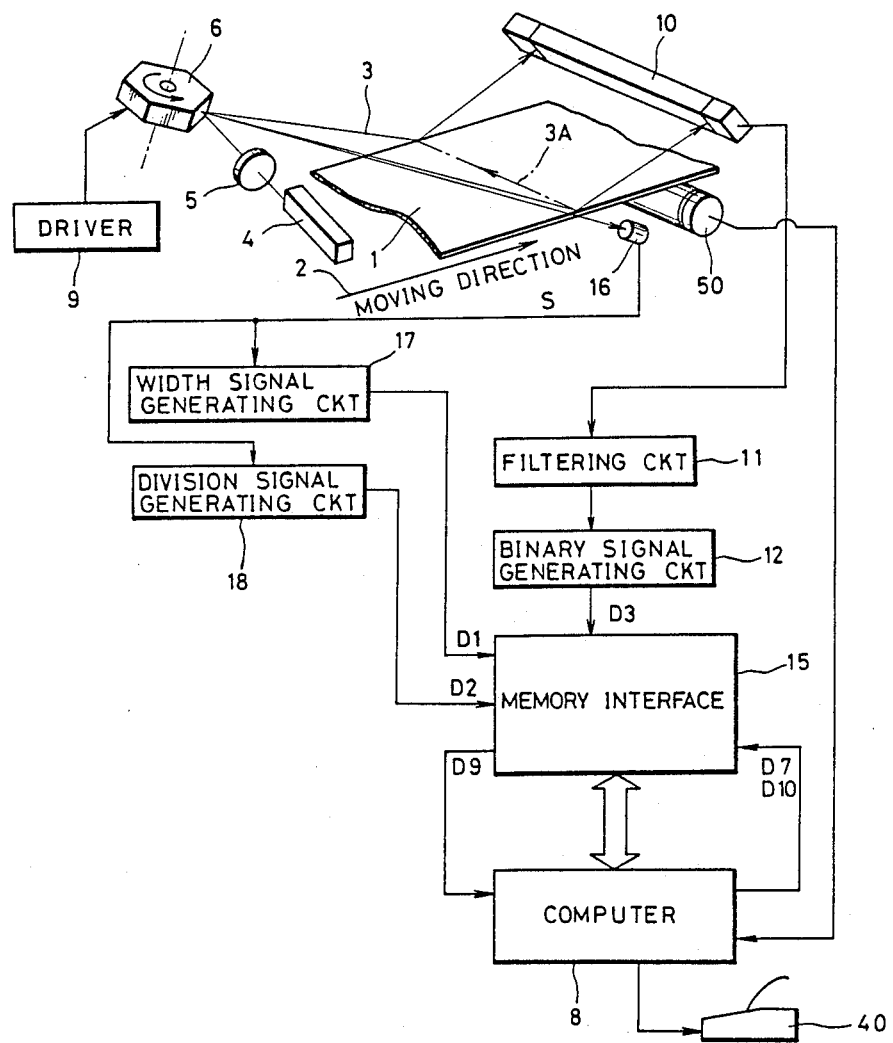
FIG. 1 is a diagram showing a surface inspection apparatus according to the present invention.

Referring now to FIG. 1 showing a surface inspection apparatus to which the present invention is applied, a web material 1 to be inspected is transported lengthwise at a constant speed of movement, namely in a direction shown by an arrow 2. While the web material 1 moves lengthwise, a laser beam 3 scans the upper surface of the web material 1 transversely, namely in the direction of the width of the web material 1, from the right to the left as viewed in FIG. 1. The laser beam 3, which is generated by a laser radiation source 4, is reflected by one of mirror surfaces of a polyhedral mirror 6 rotating in a counterclockwise direction at a constant speed and focussed on the upper surface of the web material 1 by means of a focussing lens 5. The laser beam 3 moves along a line 3A on the web material 1, as a result of the counterclockwise rotation of the polyhedral mirror 6 which is caused by a driver 9.

Figure 2:
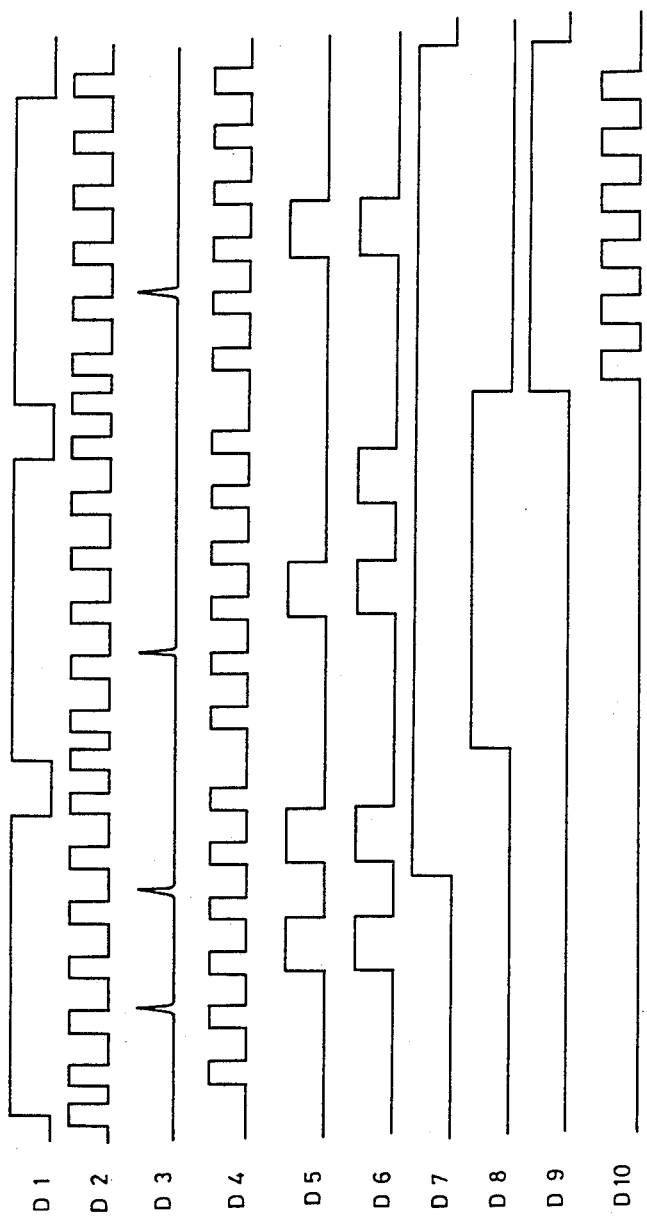
FIG. 2 shows waveforms of signals from various elements of FIG. 1.

A light receiving means such as a photo-detector 10 is disposed overhead the web material 1 to receive the laser beam 3 modulated in intensity and reflected by the upper surface of the web material 1 and provides an electric output as surface signals which are in proportion to the light intensity of the laser beam 3 received thereby and are sent to a filtering circuit 11 for filtering out noise therefrom. The surface signals are then transmitted to a binary signal generating circuit 12 for providing a binary signal of logic "0" which means that there is no surface defect in the surface of the web material 1 or logic "1" which means that there is a surface defect in the surface of the web material 1. During a single transverse scan of the web material 1, if there is detected any surface defect such as a jog, an unevenness, or an undulation with an undue thickness in comparison with a predetermined thickness, a surface signal D3 such as is shown in FIG. 2 is transferred to a memory interface 15.

Disposed out of the path of the web material 1 is a photo-detector 16 for detecting the laser beam 3 at a reference position from which scanning starts. When the photodetector 16 detects the laser beam 3, it produces a trigger signal S which actuates a width signal generating circuit 17 and a division signal generating circuit 18. This width signal generating circuit 17 generates a scanning width signal D1 shown in FIG. 2 which in turn is transmitted to the memory interface 15. On the other hand, the division signal generating circuit 18 generates dividing signals D2 in synchronism with the rotation of the polyhedral mirror 6 which in turn are also sent to the memory interface 15. These dividing signals D2, as will be described later, are specifically sent to a division signal control circuit 31 (shown in FIG. 4) of the memory interface 15 which generates lane mark pulses D4. With the lane mark pulses D4, the surface signal D3 is divided into division surface signals D5 for smaller equidistant divisions into which the web material 1 is spatially divided in the direction of the width thereof.

Figure 3:
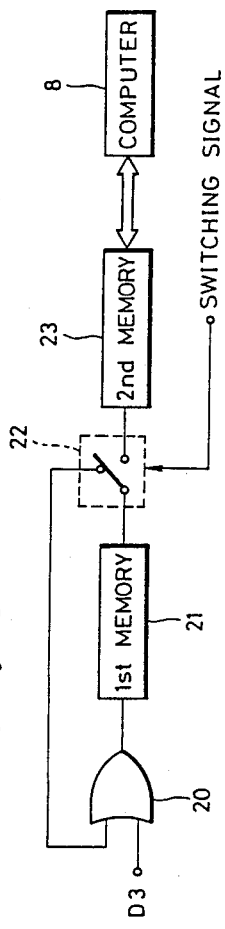
FIG. 3 is a conceptual diagram showing a memory interface incorporated in the surface inspection apparatus of FIG. 1.

The memory interface 15 basically consists of elements shown in FIG. 3. The division surface signals D5 are transmitted to first memory means 21 through an OR circuit 20 for transverse scan and memorized therein. Upon this memorization, the division surface signals D5 of the surface signal D3 are added together with division surface signals detected by the previous transverse scan and memorized in the first memory means 21 accordance with the divided portions of the width of the surface. The previously memorized division surface signals are shifted one by one and returned to the OR circuit 20 through a switching circuit 22 as the division surface signals of the surface signal D3 now detected are transmitted to the first memory means 21 one by one. Therefore, if in fact there is a binary signal, logic "1", produced by the binary signal generating circuit 12 for one portion when repeating the transverse scan N times and memorized in the first memory means 21, the first memory means 21 holds the binary signal, logic "1", therein even though the binary signals, logic "0" are transmitted thereto for the same division.

After having repeated the transverse scanning N times, a switching signal is applied to the switching circuit 22, which is thus switched to transfer the divisionally added surface signals in the first memory means 21 to a second memory means 23 by surface width portion. This second memory means 23, which is connected to a computer 8, is used as a storage section for storing analysis data from the computer 8. Upon the completion of transferring the surface signals for N transverse scans from the first to the second memory, the switching circuit 22 is returned to its initial condition shown in FIG. 3 so as to prohibit surface signals memorized in the first memory means 21 from being transferred to the second memory means 23. This prohibition is maintained during the time the computer 8 is reading out the surface signals from the second memory means 23 in order to evaluate detected surface defects.

An encoder 50 disposed below the path of the web material 1 produces line speed pulses which are transmitted to the computer 8. With reference to the line speed pulses, the computer 8 detects a predetermined number of data cells, namely a predetermined unit length of the web material to be inspected, to provide a request signal D7 which will be described later. Therefore, the transverse scan is repeated N times for the unit length of the web material 1.

Figure 4:
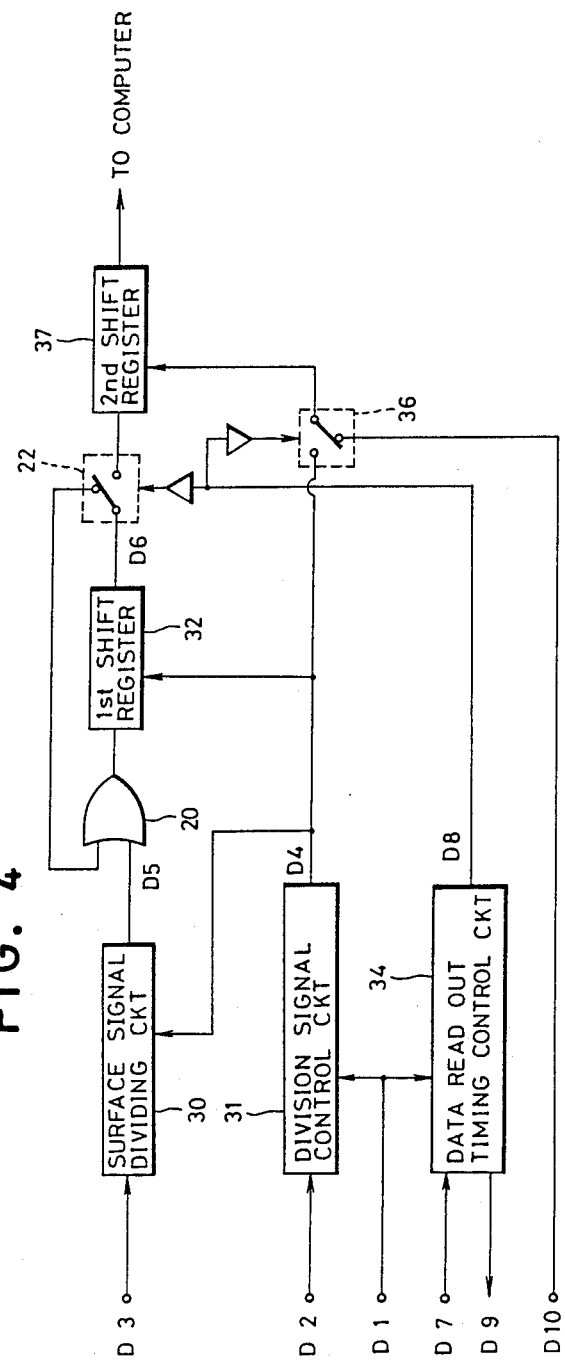
FIG. 4 is a block diagram showing an example of the memory interface incorporated in the surface inspection apparatus of FIG. 1.

Referring now to FIG. 4 showing an example of the memory interface 15, the surface signals D3 from the binary signal generating circuit 12 are transmitted to a surface signal dividing circuit 30. Simultaneously, a division signal control circuit 31 provides lane mark pulses D4 in synchronism with the transverse scanning and feeds them to the surface signal dividing circuit 30. Due to the provision of the lane mark pulses D4, the surface signal D3 is divided into the division surface signals D5 for the respective divisions of the web material 1 which are then transmitted to the first shift register 32 as the first memory means 22 through the OR circuit 20 by surface width portion. As the division signal control circuit 31 provides the lane mark pulses D4 equal in number to the number of bits of the first shift register 32 for every single transverse scan, the division surface signals D5 in the first shift register 32 are returned to the OR circuit 20 through the switching circuit 22 with the next following transverse scan.

Because the division surface signals D5 provided for N times transverse scans are added together by surface width portion in the first shift register 32 and retrieved once as surface defect data D6 therefrom, if there is a defect signal, namely a binary signal of logic "1", for any one portion or division, the defect signal is held even though no defect signal is produced for the same division upon repeating the transverse scan N times.

When the transverse scan has been repeated N times for the predetermined unit length of the web material 1, the computer 8 provides a read-out timing control circuit 34 with a request signal D7. The read-out timing control circuit 34, when receiving the request signal D7, produces a gate signal D8 in synchronism with the raising of the following scanning width signal D1 and a ready signal D9 in synchronism with the falling of the gate signal D8. During the presence of the gate signal D8, the switching circuits 22 and 36 are switched to connect the first shift registers 32 and the division mark pulse control circuit 31 to second shift register 37 as the second memory means 23. Consequently, the surface defect data D6 added together by surface width portion in the shift register 32 are transferred to the second shift register 37 by surface width portion by the aid of the lane mark pulses D4. It will be apparent that a surface signal D3 for the following part of the web material 1 is continuously transmitted to the first shift register 32 and memorized in emptied bits of the first shift register 32 by portion while the surface defect data D6 for the previous part of the web are transferred by portion to the second shift register 37.

When the surface defect data D6 for all surface width portions have been transferred to the second shift register 37 from the first shift register 32, the gate signal disappears so as to return the switching circuits 22 and 36 to their initial state shown in FIG. 4 and the computer 8, for the duration of the ready signal D9, continues to produce read-in pulse D10 which in turn are fed to the second shift register 37 through the switching circuit 36 to read the surface defect data D6 in order. Based on the surface defect data D6, the computer 8 evaluates a surface defect distribution of each division of the surface of the web material 1, thereby determining each unit length of the web material 1 to be acceptable or not. The results of this evaluation and data on the position of the scanned part of the web material 1 are printed out by means of a printer 40.

As will be apparent from the above description, since the second shift register 37 is disconnected from the first shift register 32 by means of the switching circuit 22 upon the completion of transferring the surface defect data D6 from the first to the second shift register, the computer 8 is allowed to perform several operations such as reading the transferred surface defect data D6, evaluating the surface defect data D6 and printing out the evaluated results over a relatively long period before the provision of the next request signal D7, namely the transverse scan has been repeated N times. Due to the provision of the encoder 50 which detects the unit length of the web material to allow the computer to provide the request signal, if the speed of movement of the web material is changed, the number of repetitions of the transverse scan is changed per unit length of web material according to the changed speed but no influence is exerted on the evaluation of surface defects.

Although the present invention has been fully described by way of a preferred embodiment thereof with reference to the accompanying drawings, it is to be noted that the possibility of making various change and modification will be apparent to those skilled in the art. Therefore, unless otherwise such changes and modifications depart from the true scope of the present invention, they should be construed as being included therein.

What is claimed is:

1. An apparatus for inspecting a surface of a continuously running web material by repeatedly scanning the surface in the direction of the width of said web material with a light beam, said surface modulating said light beam, said apparatus comprising:

light receiving means for receiving modulated light from said web material to provide division signals representing division of the width of the web into portions for each scan;

first memory means for adding together and storing therein said division signals for each scan in synchronism with said scanning;

second memory means for storing said added division signals by width portion;

switching means for connecting said first memory means to said second memory means to transmit said added division signals from said first to said second memory means after a predetermined number of scans has been effected; and means for reading out said added division signals by width portion from said second memory means, thereby to give an indication of surface defects on each said portion of said surface of said web material being evaluated.

2. An apparatus as defined in claim 1, wherein said first memory means is a feedback circuit of a shift register and an OR circuit.

3. An apparatus as defined in claim 2, wherein said shift register and OR circuit are connected through said switching means via a feedback loop.

4. An apparatus as defined in claim 2, wherein said second memory means is a shift register.

* * * * *